United States Patent
Wu et al.

(10) Patent No.: US 9,084,592 B2
(45) Date of Patent: Jul. 21, 2015

(54) FOCAL ABLATION ASSEMBLY

(75) Inventors: Patrick P. Wu, San Carlos, CA (US);
Cesar A. Ico, San Francisco, CA (US);
Richard S. Williams, Redwood City, CA (US)

(73) Assignee: C2 THERAPEUTICS, INC., Redwood City, CA (US)

( * ) Notice: Subject to any disclaimer, the term of this patent is extended or adjusted under 35 U.S.C. 154(b) by 991 days.

(21) Appl. No.: 13/180,450

(22) Filed: Jul. 11, 2011

(65) Prior Publication Data

US 2013/0018367 A1     Jan. 17, 2013

(51) Int. Cl.
*A61B 18/02* (2006.01)
*A61B 18/00* (2006.01)

(52) U.S. Cl.
CPC ..... *A61B 18/0218* (2013.01); *A61B 2018/0022* (2013.01); *A61B 2018/00494* (2013.01); *A61B 2018/00577* (2013.01); *A61B 2018/00982* (2013.01)

(58) Field of Classification Search
CPC ........... A61B 18/02; A61B 2018/0212; A61B 2018/0262; A61B 2018/00982
USPC ............................. 606/21, 23; 607/116, 127
See application file for complete search history.

(56) References Cited

U.S. PATENT DOCUMENTS

| | | | |
|---|---|---|---|
| 6,027,499 A * | 2/2000 | Johnston et al. | 606/22 |
| 6,283,959 B1 | 9/2001 | Lalonde et al. | |
| 6,355,029 B1 | 3/2002 | Joye et al. | |
| 6,383,181 B1 * | 5/2002 | Johnston et al. | 606/24 |
| 6,468,297 B1 | 10/2002 | Williams et al. | |
| 6,551,274 B2 | 4/2003 | Heiner | |
| 6,908,462 B2 | 6/2005 | Joye et al. | |
| 7,189,227 B2 | 3/2007 | Lafontaine | |
| 8,021,362 B2 * | 9/2011 | Deem et al. | 606/41 |
| 2002/0010460 A1 | 1/2002 | Joye et al. | |
| 2002/0026182 A1 | 2/2002 | Joye et al. | |

(Continued)

FOREIGN PATENT DOCUMENTS

RU     2178999 C2     2/2002

OTHER PUBLICATIONS

Oct. 11, 2012 International Search Report in PCT/US2012/045952, 8pp.

(Continued)

*Primary Examiner* — Joseph Stoklosa
*Assistant Examiner* — Jocelyn D Ram
(74) *Attorney, Agent, or Firm* — Haynes Beffel & Wolfeld LLP; James F. Hann

(57) ABSTRACT

A focal ablation assembly, used with an endoscope comprising an endoscopic tube, comprises a cryogenic catheter, a balloon and a reinforcing element. The cryogenic catheter is placeable within the endoscopic tube channel and has a distal end placeable at the distal end of the endoscopic tube. The balloon is mountable to the catheter distal end and extends distally of both of the distal ends. The reinforcing element at least partially defines the shape of the balloon in the expanded state. The balloon defines a balloon volume when expanded and has a thermally conductive therapeutic region which provides effectively no thermal insulation. In some examples the focal ablation assembly comprises a delivery catheter extending along the channel with a distal portion fluidly coupled to the balloon interior, whereby refrigerant can be introduced into the balloon interior and towards the therapeutic region by the delivery catheter.

11 Claims, 15 Drawing Sheets

(56) References Cited

U.S. PATENT DOCUMENTS

| | | | |
|---|---|---|---|
| 2002/0045894 A1 | 4/2002 | Joye et al. | |
| 2002/0099365 A1 | 7/2002 | Joye et al. | |
| 2002/0143323 A1* | 10/2002 | Johnston et al. | 606/21 |
| 2002/0151880 A1 | 10/2002 | Lafontaine | |
| 2002/0183731 A1 | 12/2002 | Holland et al. | |
| 2003/0036752 A1 | 2/2003 | Joye et al. | |
| 2003/0060762 A1 | 3/2003 | Zvuloni et al. | |
| 2003/0109912 A1 | 6/2003 | Joye et al. | |
| 2004/0143249 A1* | 7/2004 | Lafontaine | 606/21 |
| 2006/0030843 A1* | 2/2006 | Lane et al. | 606/21 |
| 2006/0212027 A1 | 9/2006 | Marrouche et al. | |
| 2007/0299433 A1* | 12/2007 | Williams et al. | 606/21 |
| 2008/0009851 A1* | 1/2008 | Wittenberger et al. | 606/40 |
| 2008/0058591 A1 | 3/2008 | Saadat et al. | |
| 2008/0312644 A1* | 12/2008 | Fourkas et al. | 606/22 |
| 2009/0182319 A1* | 7/2009 | Lane et al. | 606/21 |
| 2009/0299355 A1 | 12/2009 | Bencini et al. | |
| 2010/0057065 A1 | 3/2010 | Krimsky | |
| 2010/0121270 A1* | 5/2010 | Gunday et al. | 604/98.01 |
| 2010/0130970 A1 | 5/2010 | Williams et al. | |
| 2011/0184400 A1* | 7/2011 | Pageard | 606/21 |
| 2012/0283713 A1* | 11/2012 | Mihalik et al. | 606/21 |
| 2012/0283714 A1* | 11/2012 | Mihalik et al. | 606/21 |
| 2012/0283715 A1* | 11/2012 | Mihalik et al. | 606/21 |
| 2012/0289951 A1* | 11/2012 | Kassab et al. | 606/21 |
| 2013/0197497 A1* | 8/2013 | Wittenberger et al. | 606/21 |
| 2013/0197499 A1* | 8/2013 | Lalonde et al. | 606/21 |

OTHER PUBLICATIONS

Extended EP Search Report from corresponding EP Application No. 12811731.4, Feb. 23, 2015; 9 pgs.

* cited by examiner

FOCAL ABLATION ASSEMBLY

CROSS-REFERENCE TO OTHER APPLICATIONS

This application is related to the following US patent application publication: US 2010/0130970 A1.

FEDERALLY SPONSORED RESEARCH OR DEVELOPMENT

None.

BACKGROUND OF THE INVENTION

Throughout the GI tract in the human body there are focal lesions of unwanted or unhealthy tissue that physicians desire to remove or ablate in situ. Examples of these lesions include 'islands' of intestinal metaplasia and dysplasia in the esophagus or 'flat' polyps in the colon. Removal of these tissues through techniques such as Endoscopic Mucosal Resection (EMR) may create unwanted complications such as bleeding and current ablative modalities such as Argon Plasma Coagulation (APC) and Radio Frequency Ablation (RFA) suffer from a variety of drawbacks. Furthermore, existing cryoablation technologies, which spray the cryogen directly onto the body lumen do not adequately allow control of the energy dosage.

BRIEF SUMMARY OF THE INVENTION

An example of a focal ablation assembly is used with an endoscope comprising an endoscopic tube having proximal and distal ends and defining a channel extending between the proximal and distal ends. The focal ablation assembly comprises a cryogenic catheter, a balloon and a reinforcing element. The cryogenic catheter is placeable within the channel. The cryogenic catheter defines a catheter lumen and has a distal end placeable at the distal end of the endoscopic tube. The balloon is mountable to at least one of the distal end of the endoscopic tube and the distal end of the catheter. The balloon extends distally of both of the distal ends of the endoscopic tube and the cryogenic catheter. The reinforcing element at least partially defines the shape of the balloon in the expanded state. The balloon defines a balloon volume when in the expanded state. The balloon comprises a thermally conductive therapeutic region, the thermally conductive therapeutic region providing effectively no thermal insulation. In some examples the therapeutic region comprises a flexible, tissue-conformable therapeutic region. In some examples the thermal conductivity of the balloon is greater at the therapeutic region than at a portion of the remainder of the balloon. In some examples the focal ablation assembly comprises a delivery catheter extending along the channel with a distal portion fluidly coupled to the balloon interior, whereby refrigerant can be introduced into the balloon interior and towards the therapeutic region by the delivery catheter. In some examples the reinforcing elements are formed integrally with the balloon. In some examples the reinforcing elements comprise at least two spaced-apart support wires extending at least part way along the balloon interior. In some examples the reinforcing elements cause the balloon to have a flattened cross-sectional shape in the expanded state.

An example of a focal ablation system comprises an endoscope and a focal ablation assembly. The endoscope comprises an endoscopic tube having proximal and distal ends and defines a channel extending between the proximal and distal ends. The focal ablation assembly comprises a cryogenic catheter, a balloon, and a reinforcing element. The cryogenic catheter is located within the channel and defines a catheter lumen. The cryogenic catheter has a distal end at the distal end of the endoscopic tube. The balloon is mounted to the distal end of the catheter with the balloon extending distally of both of the distal ends of the endoscopic tube and the cryogenic catheter. The balloon is placeable in collapsed and expanded states and has a balloon interior. The reinforcing element at least partially defines the shape of the balloon in the expanded state. The balloon defines a balloon volume when in the expanded state. The balloon comprises a flexible, tissue-conformable, thermally conductive therapeutic region, the thermally conductive therapeutic region providing effectively no thermal insulation. Some examples of the focal ablation system include a delivery catheter extending along the channel and having a distal portion fluidly coupled to the balloon interior, whereby refrigerant can be introduced into the balloon interior and towards the therapeutic region by the refrigerant delivery catheter. Some examples of the focal ablation system include an exhaust lumen within at least one of (1) the channel of the endoscopic tube, and (2) the catheter lumen.

Other features, aspects and advantages of the present invention can be seen on review the figures, the detailed description, and the claims which follow.

BRIEF DESCRIPTION OF THE DRAWINGS

FIGS. 1A-10A are directed to a first type of a focal ablation system according to a first aspect of the invention.

FIG. 2 is a simplified enlarged cross-sectional view of the distal end of one example of the system of FIG. 1A showing a cryogenic catheter passing through the channel of an endoscopic tube with a cap mounted to the distal end of the endoscopic tube, the cap having a thermally conductive therapeutic region located at the distal end of the cap.

FIG. 3 is a view similar to that of FIG. 2 of an alternative example of the system of FIG. 1A in which the therapeutic region is along a sidewall of the cap.

FIG. 4 is a view similar to that of FIG. 2 wherein the cap is mounted to the distal end of the cryogenic catheter instead of the endoscopic tube as shown in FIG. 1B.

FIG. 6 illustrates an example in which the therapeutic region has a convex outer surface.

FIG. 10A is a view along line 10A-10A of FIG. 10.

FIG. 10 shows an example of a cap similar to the cap of FIG. 2 but in which the cap has an extension defining an exhaust lumen coaxial with the endoscopic tube.

FIG. 11 shows an example of a balloon type focal ablation system in which an elastomeric balloon is mounted to the distal end of the cryogenic catheter and expands within the cap, a portion of the balloon forming a barrier to the refrigerant along the therapeutic region at the distal end of the cap.

FIGS. 12 and 12A are simplified side and end cross-sectional views of a balloon type focal ablation system in which a balloon type focal ablation assembly is used with an endoscopic tube, the balloon being mounted to the distal end of a cryogenic catheter, the cryogenic catheter passing through the channel of the endoscopic tube, the therapeutic region being along a sidewall of the balloon. FIG. 12A shows the use of reinforcing elements within the balloon to cause the balloon to have a flattened or oval cross-sectional shape to better conform to the sidewall of the body lumen.

FIGS. 13 and 13A are simplified side and end cross-sectional views of a focal ablation balloon and reinforcing elements similar to those of FIGS. 12 and 12A.

FIG. 14 illustrates another example of a balloon type focal ablation system in which the distal end of a reinforcing element extends through the delivery catheter and is secured to the distal portion of the balloon.

FIG. 15 shows a further example of a balloon type focal ablation system comprising a balloon type cap.

DETAILED DESCRIPTION OF THE INVENTION

Figure 1A:
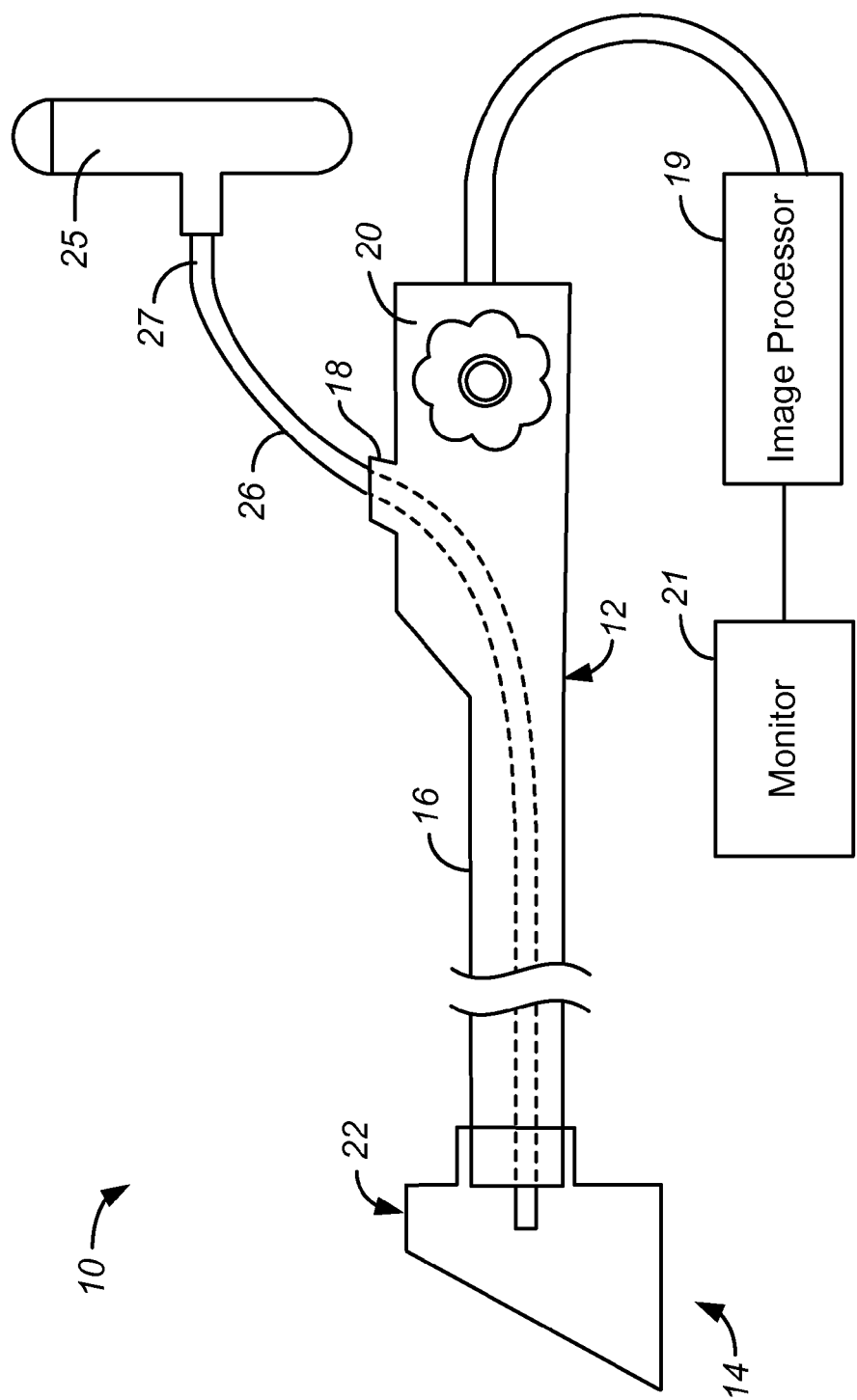
FIGS. 1A and 1B are overall views showing focal ablation systems made according to the invention.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

The control of three primary factors is necessary for repeatable cryoablation via evaporative cooling. These factors are evaporation temperature of the cryogen, the mass flow rate of the cryogen/surface area, and the amount of time that the cryogen is applied. The present invention directly addresses two of these factors. (1) Evaporation temperature of the cryogen is set by controlling the evaporation pressure. The evaporation pressure can be controlled by appropriately sizing the cryogenic refrigerant delivery and exhaust lumens. (2) The mass flow rate/surface area can be controlled by appropriately sizing the cryogenic refrigerant delivery lumen (to control mass flow rate) and defining a fixed treatment area either by physically defining a treatment area or by controlling distribution of the cryogen delivery onto a treatment surface.

Figure 1B:
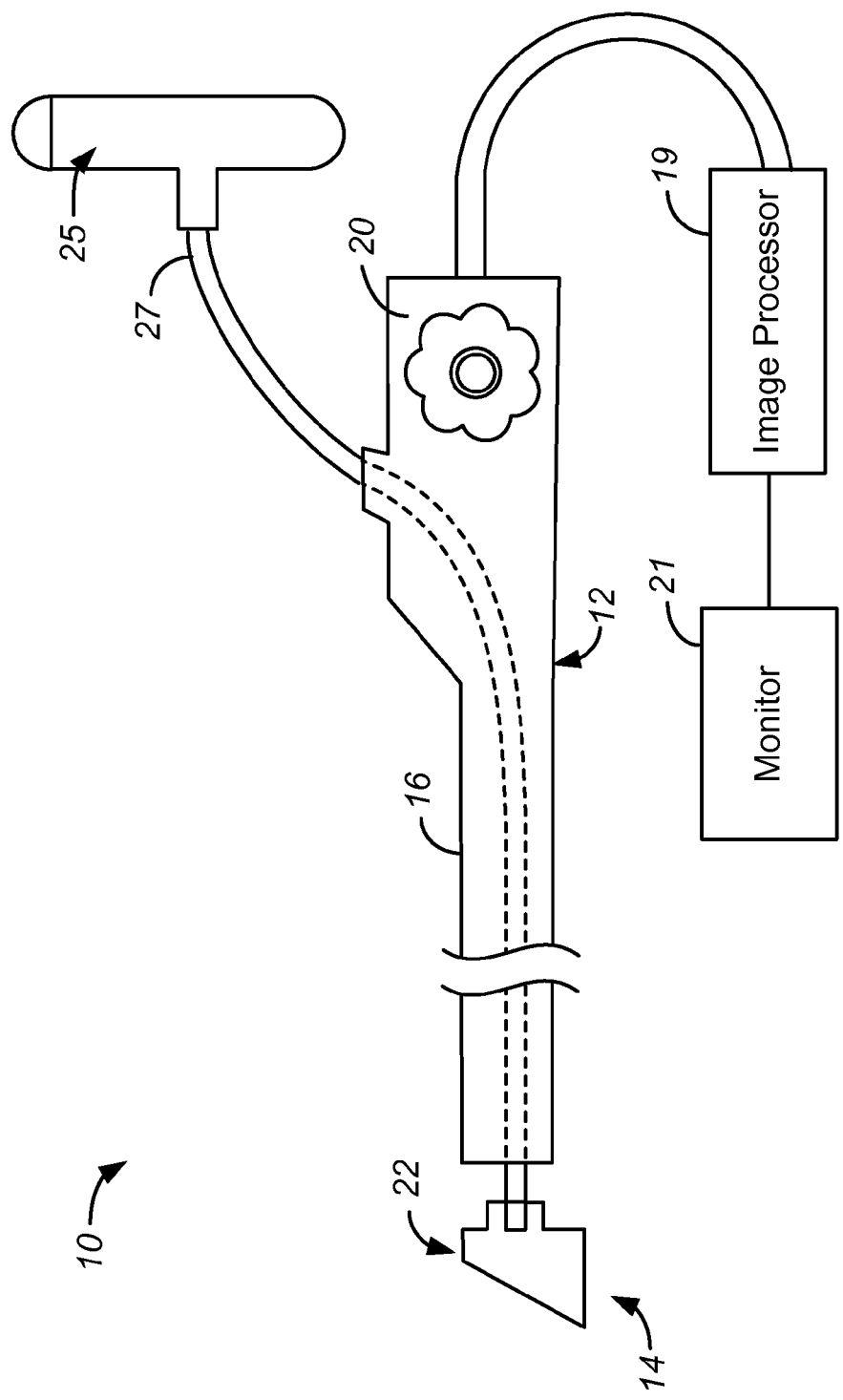

FIG. 1A is an overall view showing a generalized example of a focal ablation system 10 including broadly an endoscope 12 and a focal ablation assembly 14. Endoscope 12 includes an endoscopic tube 16 having an accessory channel port 18 at a proximal end 20 of endoscopic tube 16 and a cap 22 at the distal end 24 of endoscopic tube 16. Endoscope 12 may be a conventional endoscope such as Olympus GIF-140 or GIF-Q160Z, that connects to an image processor 19, which then displays the image on monitor 21. FIG. 1B is similar to FIG. 1A but shows cap 22 mounted to the distal end 34 of cryogenic catheter 26 instead of endoscopic tube 16.

FIGS. 2-10A are directed to a first type of a focal ablation system 10 according to a first aspect of the invention. Focal ablation assembly 14, see FIGS. 1 and 2, includes a cap 22 mounted to the distal end 24 of an endoscopic tube 16 and a cryogenic catheter 26 passing through the channel 28 of endoscopic tube 16. Focal ablation assembly 14 also includes a cryoablation controller 25 at the proximal end of 27 of cryogenic catheter 26. In some examples, described below with reference to FIGS. 1B and 4, cap 22 can be mounted to the distal end 34 of cryogenic catheter 26. Cap 22 in FIG. 2 has a generally cylindrical cross-sectional shape and defines a centerline 30. Cap 22 has a distal end 32 extending distally of the distal end 24 of endoscopic tube 16 and the distal end 34 of cryogenic catheter 26. In this example cap 22 is oriented obliquely to centerline 30 to facilitate tissue apposition. Cryogenic catheter 26 defines a catheter lumen 29 through which a delivery catheter 31 passes. As is discussed in more detail below, distal end 32 of cap 22 will be placed against tissue at the target site to be treated.

Cap 22 is preferably of a clear, semi-rigid, soft, flexible material, or a combination of materials, such as a polymer material, so to substantially maintain its shape during use while not causing tissue trauma. Examples of the material for 22 include silicone, polyurethane, polyvinyl chloride, and C-Flex®, a thermoplastic elastomer, specifically styrene-ethylene-butylene modified block copolymer with silicone oil. Cap 22 may be manufactured by, for example, injection molding, casting, or thermoforming. Distal end 32 of cap 22 defines a thermally conductive therapeutic region 36 having a typical cross-sectional area of 0.5 cm$^2$ to 3.0 cm$^2$. In this example therapeutic region 36 is covered by a cover 38 of a thin transparent polymer, such as polyurethane having a thickness of typically less than 0.05 mm (0.002 inch). In this way the liquid refrigerant 40 passing through the delivery lumen of delivery catheter 31 and out through the exit opening 41 of delivery catheter 31 does not contact tissue outside the target site but rather heat is removed from the tissue at the target site as the liquid refrigerant evaporates while in contact with cover 38. Although polyurethane may not be considered to be highly thermally conductive, the thinness of cover 38 allows cover 38 to provide effectively no thermal insulation between the evaporating liquid refrigerant and the target tissue. In addition, it is preferable that cover 38 be transparent or at least translucent so that the physician can see what is happening to the tissue at the target site. The selection of the size of therapeutic region 36 is typically chosen according to the size of the treatment site or the desired mass flow rate/surface area for refrigerant 40, or both. Evaporated refrigerant 42 passes out of cap volume 39 through catheter lumen 29 between delivery catheter 31 and the inner wall of cryogenic catheter 26.

Cover 38 is stated to provide effectively no thermal insulation between the evaporating liquid refrigerant and the target tissue. In this application the phrase effectively no thermal insulation is meant to mean that tissue necrosis can occur at the target site upon the application of a cryogenically ablative liquid refrigerant, such as nitrous oxide (N2O), to the surface of cover 38.

Cryogenic catheter 26 may be sized appropriately for introduction through, for example, 2.0 mm, 2.8 mm or 3.7 mm diameter instrument channels 28. Cryogenic catheter 26 may be constructed from materials such as PEBAX or nylon. Delivery catheter 31 may be constructed from a rigid polymer such as polyimide or a metal such as stainless steel, sufficient to withstand internal pressure approaching 1000 psig. The diameter of delivery lumen 44 defined by delivery catheter 31 is typically in the range of 0.15 mm (0.006 inch) to 0.30 mm (0.012 inch). The diameter of delivery lumen 44 can be chosen according to the desired mass flow rate/surface area for refrigerant 40 contacting therapeutic region 36.

Figure 2:
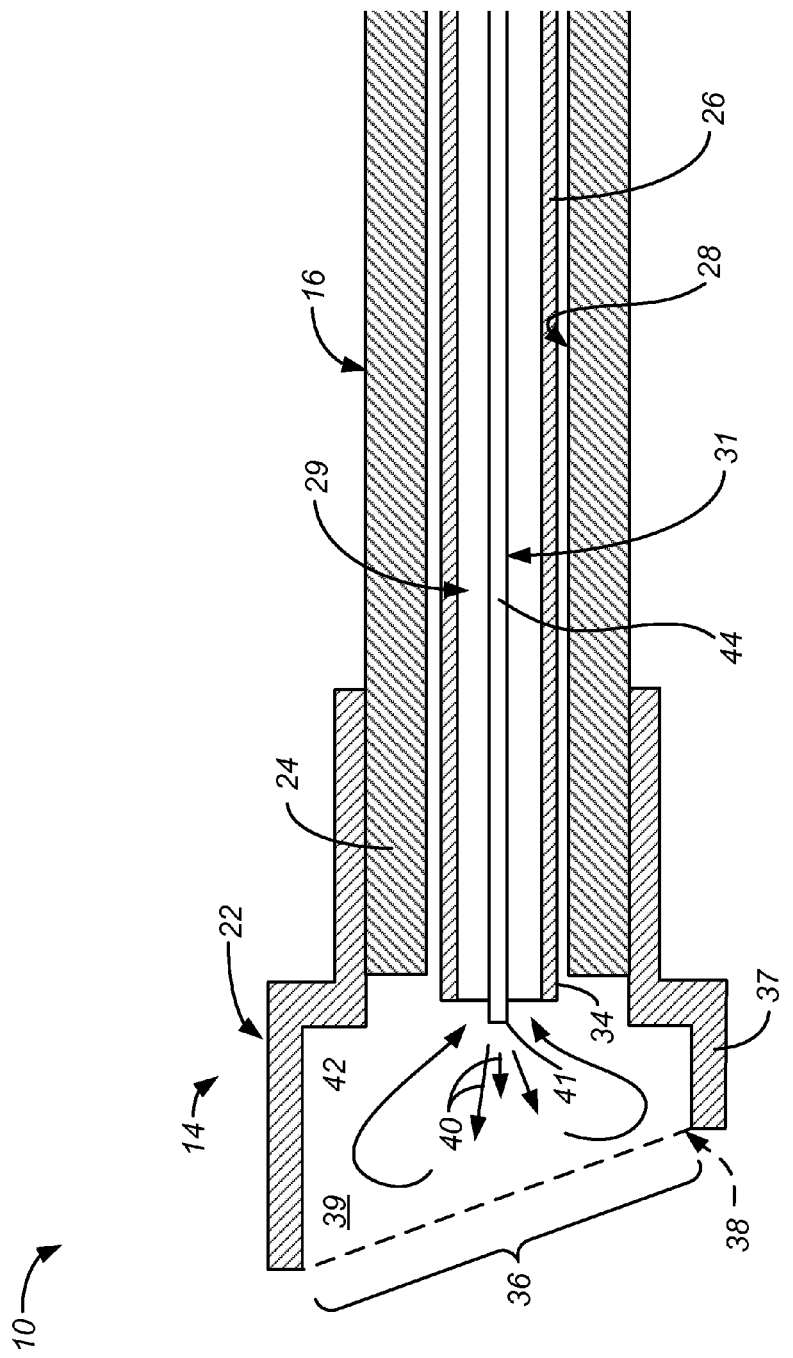
Figure 3:
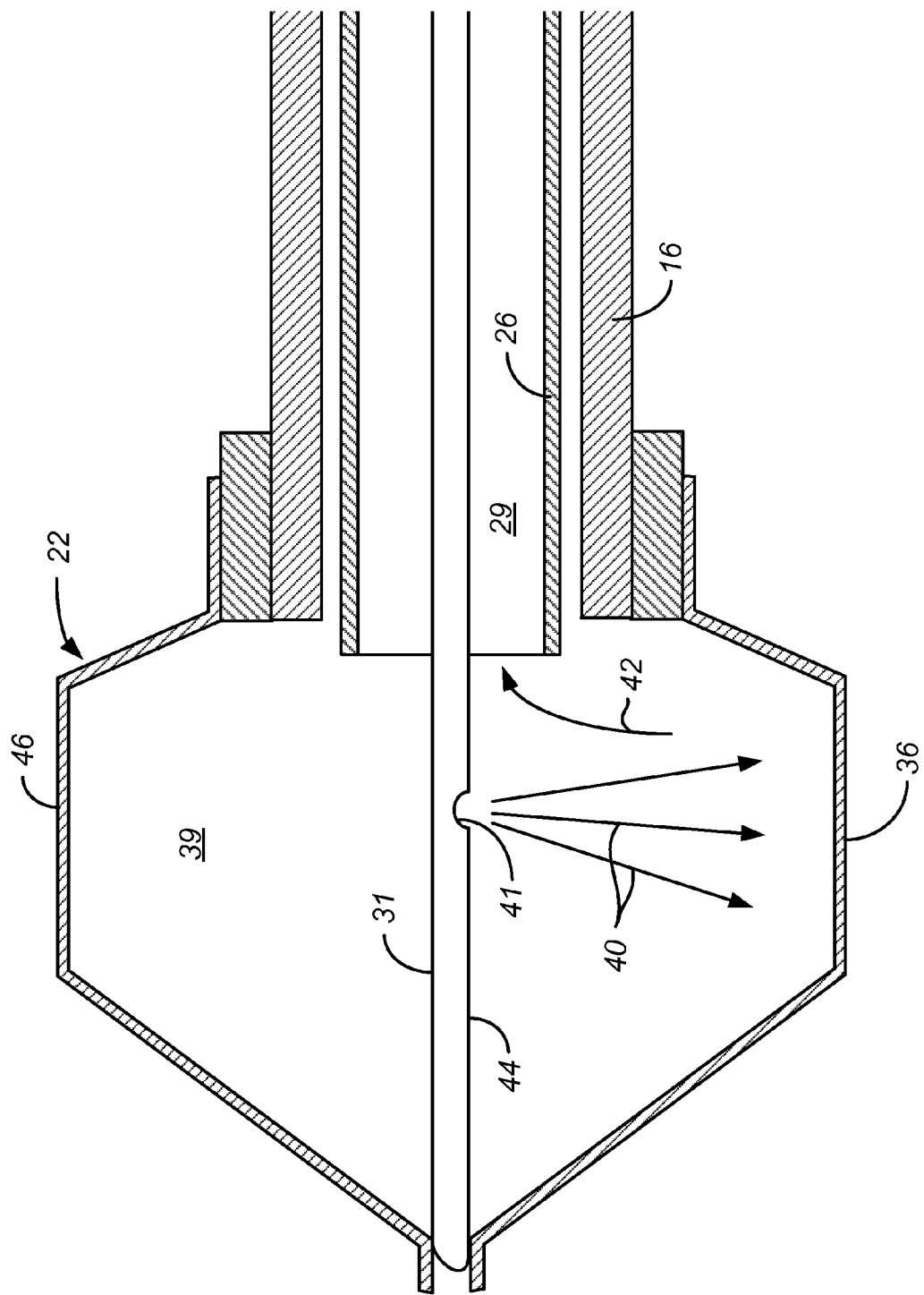

FIG. 3 is a view similar to that of FIG. 2 of an alternative example of the focal ablation system 10 of FIG. 1 in which the therapeutic region 36 is along a sidewall 46 of the cap. Delivery catheter 31 extends completely through cap volume 39 and is secured to a distal end of cap 22. Delivery catheter 31 has a laterally oriented exit opening 41 positioned opposite the therapeutic region 36 along sidewall 46 of cap 22. This feature permits liquid refrigerant 40 to be directed against sidewall 46 at therapeutic region 36 so the target tissue at the target treatment site 78 against which therapeutic region 36 is pressing, see FIG. 12, can be thermally ablated due to the low temperature of the liquid refrigerant.

Figure 4:
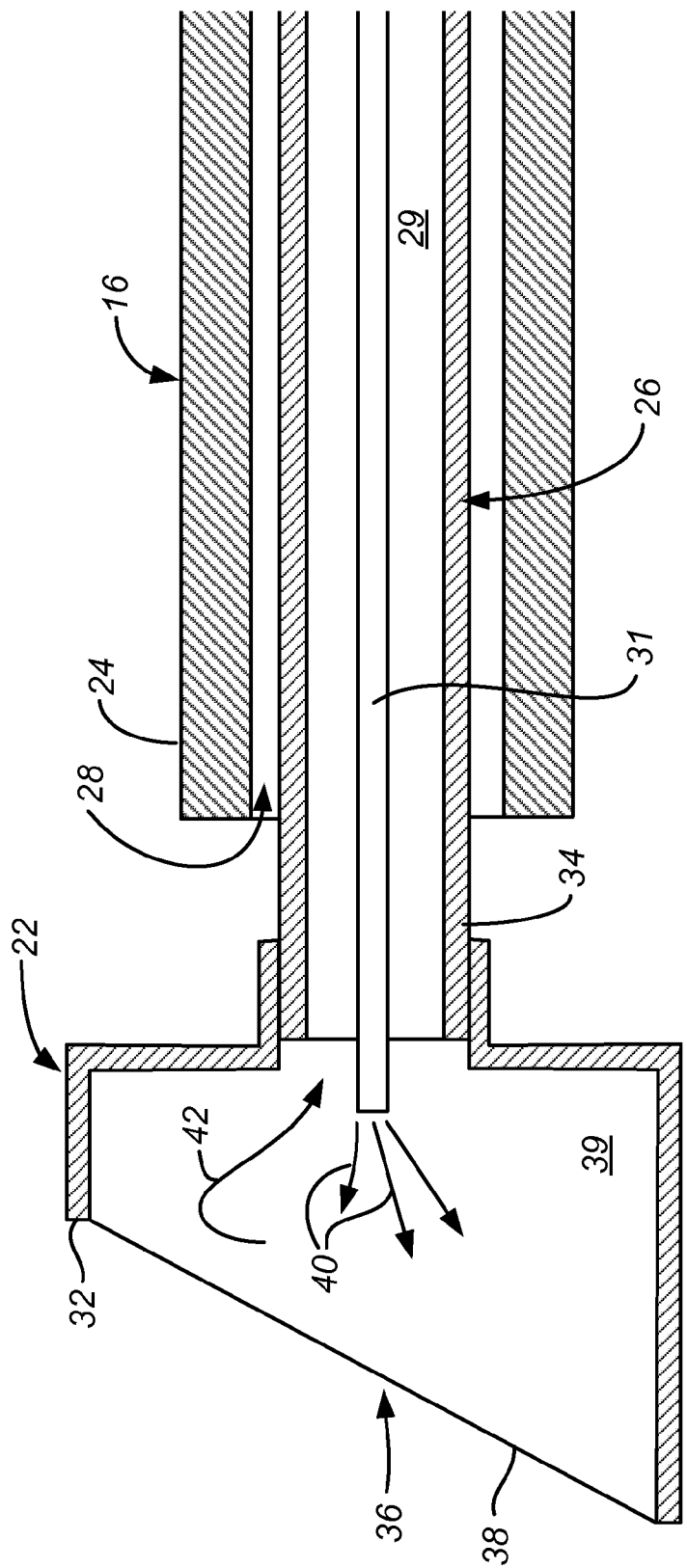

FIG. 4 is a view similar to that of FIG. 2 wherein the cap 22 is mounted to the distal end 34 of the cryogenic catheter 26 instead of the endoscopic tube 16. See also FIG. 1B.

Figure 5A:
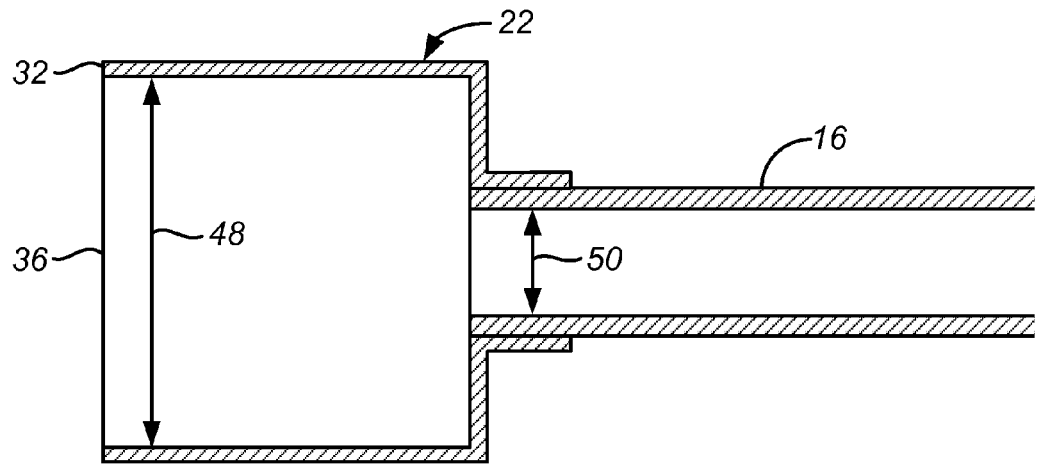
FIGS. 5A-5C are simplified cross-sectional views of examples of three different caps in which the cross-sectional area of the therapeutic region at the distal end of each cap is different while the cross-sectional area of the endoscopic tube to which it is mounted remains the same.
Figure 5B:
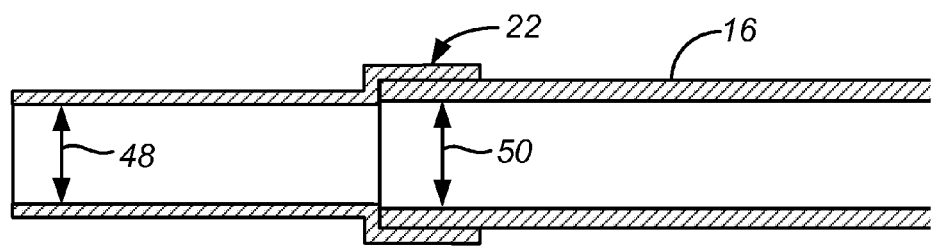
Figure 5C:
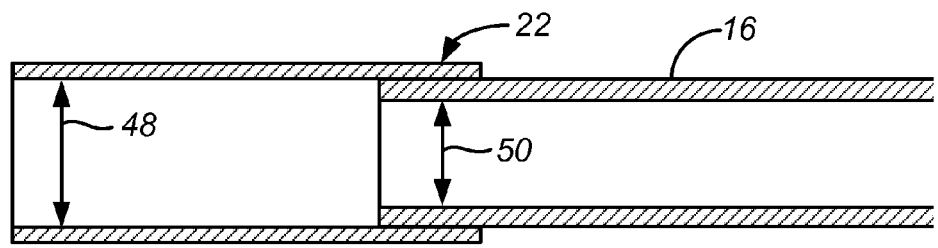

FIGS. 5A-5C are simplified cross-sectional views of examples of three different caps 22 in which the cross-sectional area 48 of the therapeutic region 36 at the distal end 32 of each cap 22 is different while the cross-sectional area 50 of the endoscopic tube 16 to which it is mounted remains the same. This concept is used to allow the physician to choose the appropriately sized cap 22 according to the size of the target site, or the mass flow rate/surface area of refrigerant 40, or both.

Figure 6:
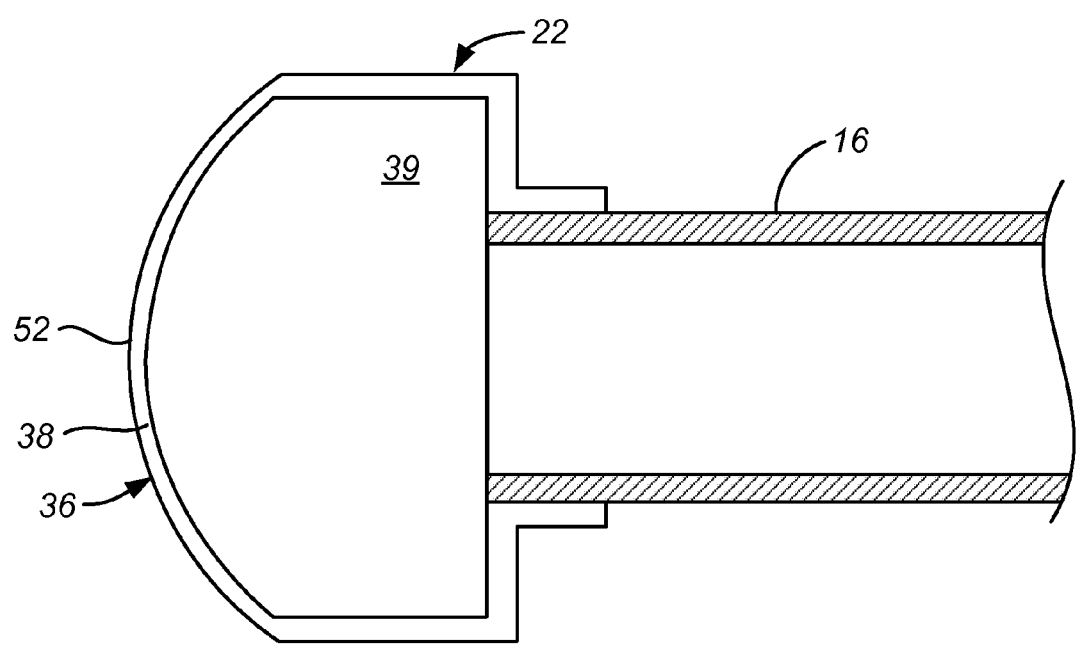
Figure 7A:
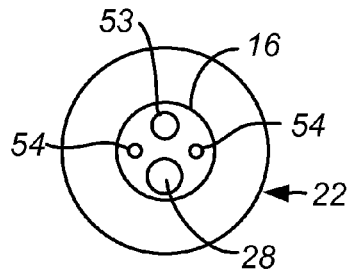
FIGS. 7A, 8A and 9A are simplified end views showing caps having round, generally oval and rectangular cross-sectional shapes, respectively, each mounted to the distal end of an endoscope, each Fig. illustrating a conventional endoscope having, in this example, a camera, two lights for illumination and a working channel.
Figure 8A:
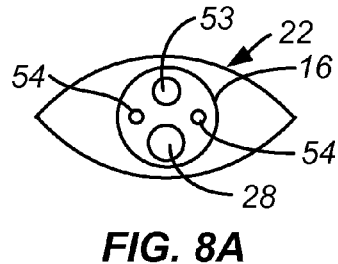
Figure 9A:
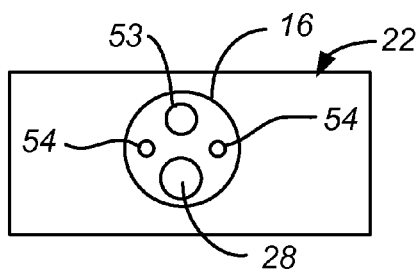

FIG. 6 illustrates an example in which the therapeutic region 36 has a convex outer surface 52. This configuration may be useful to improve the amount of contact between the therapeutic surface of the cap and the target tissue. FIGS. 7A, 8A and 9A are simplified end views showing caps 22 having round, generally oval and rectangular cross-sectional shapes, respectively. Each cap 22 is mounted to the distal end 24 of an endoscopic tube 16. Each figure illustrates a conventional endoscope 12 having, in this example, a camera 53, two lights 54 for illumination and a working channel 28.

Figure 7B:
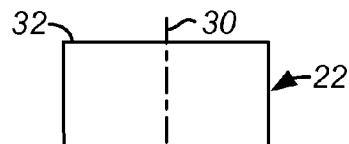
FIGS. 7B, 8B and 9B show the caps of FIGS. 7A, 8A and 9A having distal ends oriented perpendicular to the centerlines of the respective caps.
Figure 8B:
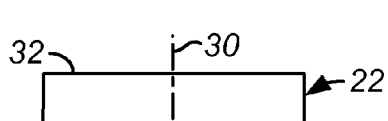
Figure 7C:
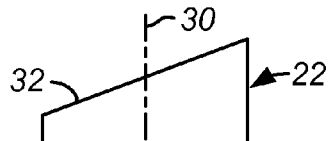
FIGS. 7C, 8C and 9C show the caps of FIGS. 7A, 8A and 9A having distal ends oriented obliquely to the centerlines of the respective caps.
Figure 8C:
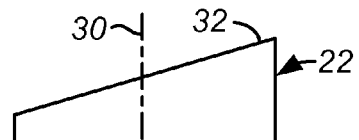
Figure 9B:
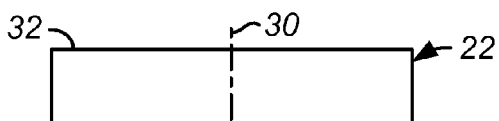
Figure 9C:
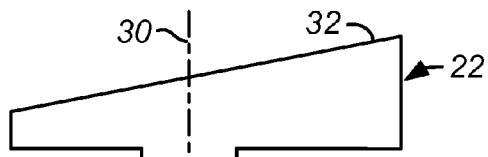

FIGS. 7B, 8B and 9B show the caps 22 of FIGS. 7A, 8A and 9A having distal ends 32 oriented perpendicular to the centerlines 30 of the respective caps. FIGS. 7C, 8C and 9C show the caps 22 of FIGS. 7A, 8A and 9A having distal ends 32 oriented obliquely to the centerlines 30 of the respective caps.

Figure 10:
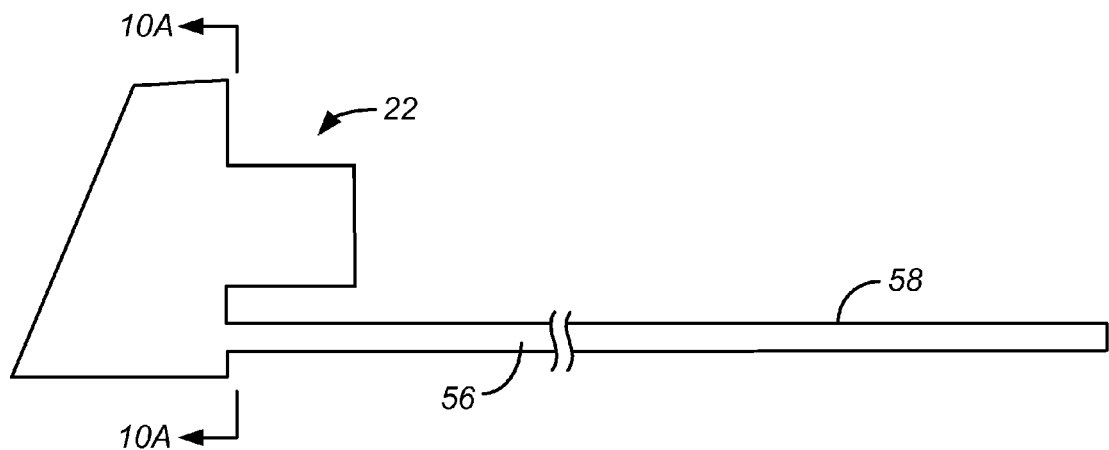
Figure 10A:
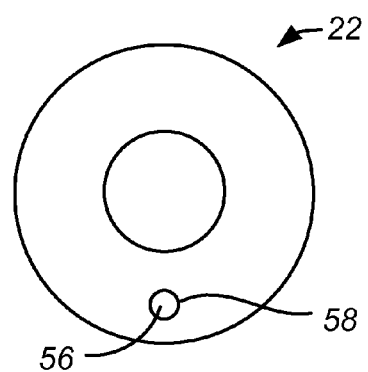

FIGS. 10 and 10A show an example of cap 22 similar to the cap 22 of FIG. 2 but in which an exhaust lumen 56 is defined by a coaxial extension 58 of cap 22. Extension 58 will lie generally parallel to the endoscopic tube 16. This permits a larger cross-sectional area for the exhaust lumen than would be typically available if the exhaust lumen was defined by an accessory channel of endoscopic tube 16. Exhaust lumen 56 is typically in the range of 2-5 mm in diameter. The cross-sectional areas provided by catheter lumen 29 when used as exhaust lumens in the above examples are typically of a similar size.

Figure 11:
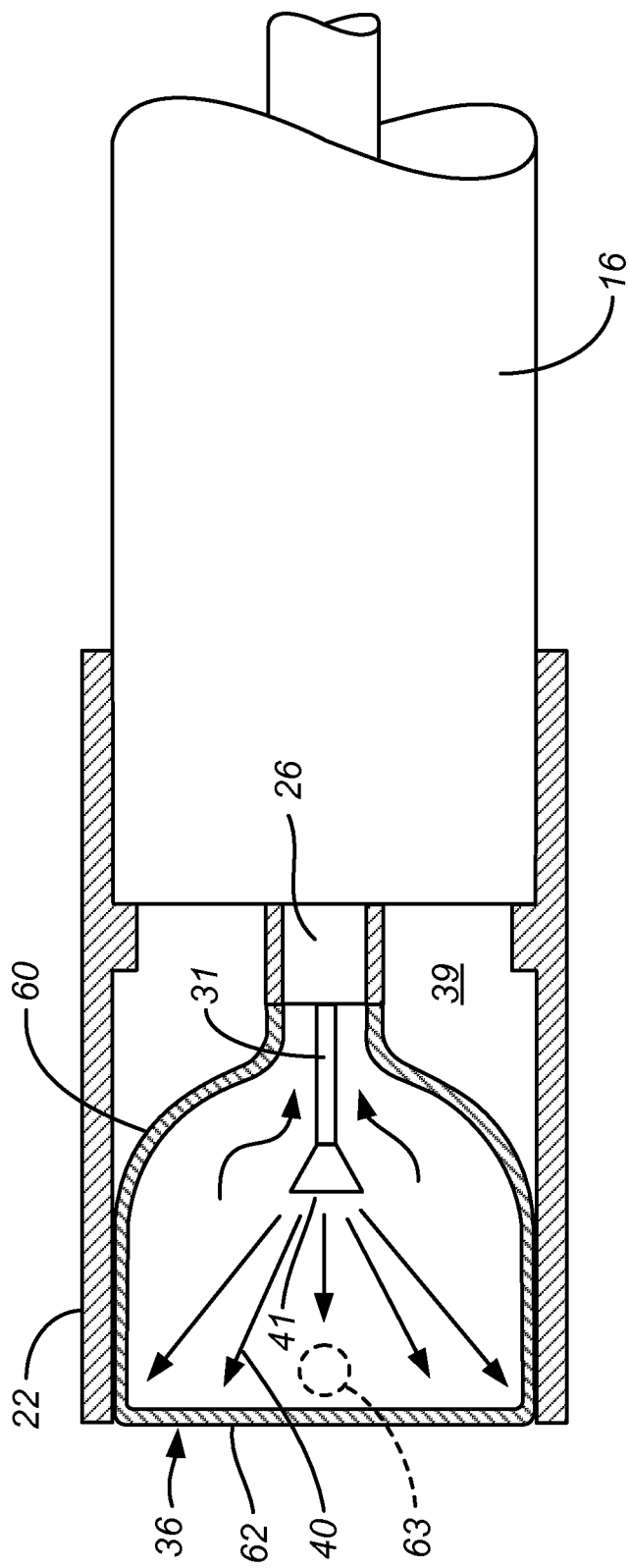
FIGS. 11-15 show balloon-type of focal ablation systems according to a second aspect of the invention.

FIG. 11 shows another example in which an elastomeric balloon 60 is mounted to the distal end 34 of the cryogenic catheter 26. Balloon 60 expands within the cap volume 39 of cap 22 with a portion 62 of the balloon forming the cover 38 along the therapeutic region 36 at the distal end 32 of the cap. A vent hole 63 is formed in the sidewall 46 of cap 22 to facilitate the expansion of balloon 60.

In use, the physician will typically select a cap 22 having the appropriate size and shape for the particular target treatment site 78. The size of therapeutic region 36 may also be chosen according to the desired mass flow rate/surface area for refrigerant 40. Assuming the focal ablation system 10 of FIG. 2 is being used, cap 22 can be installed on the distal end 24 of endoscopic tube 16. Cryogenic catheter 26, typically with delivery catheter 31 therein, can be placed through accessory port 18 of the endoscope 12 and passes through channel 28 of the endoscopic tube 16 until the distal end 34 of cryogenic catheter 26 is at cap volume 39. Note that the installation of cap 22 could occur after positioning cryogenic catheter 26 within endoscope 12. The distal portion of focal ablation system 10 is placed in the patient so that region 36 is properly positioned at the target treatment site 78. The refrigerant from cryoablation controller 25 is then directed through delivery catheter 31 and against cover 38 at to the target treatment site 78. The evaporation of the refrigerant on cover 38 lowers the temperature of the tissue at the target treatment site enough to cause necrosis of the tissue. The evaporated refrigerant 42 passes out of cap volume 39 through catheter lumen 29.

FIGS. 12-15 show balloon type of focal ablation systems, somewhat different from the focal ablation system of FIGS. 1-11, according to a second aspect of the invention.

Figure 12:
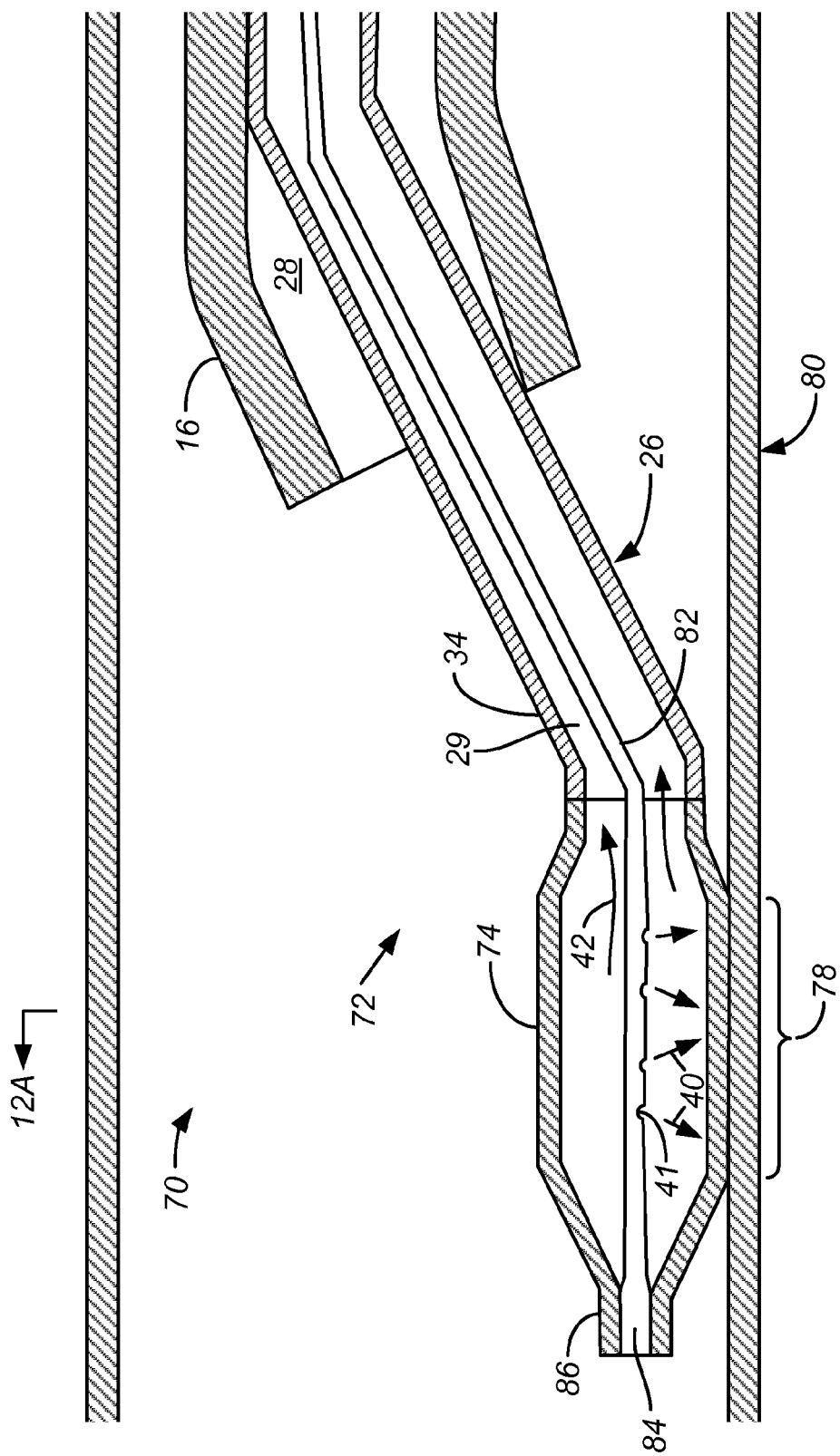
Figure 12A:
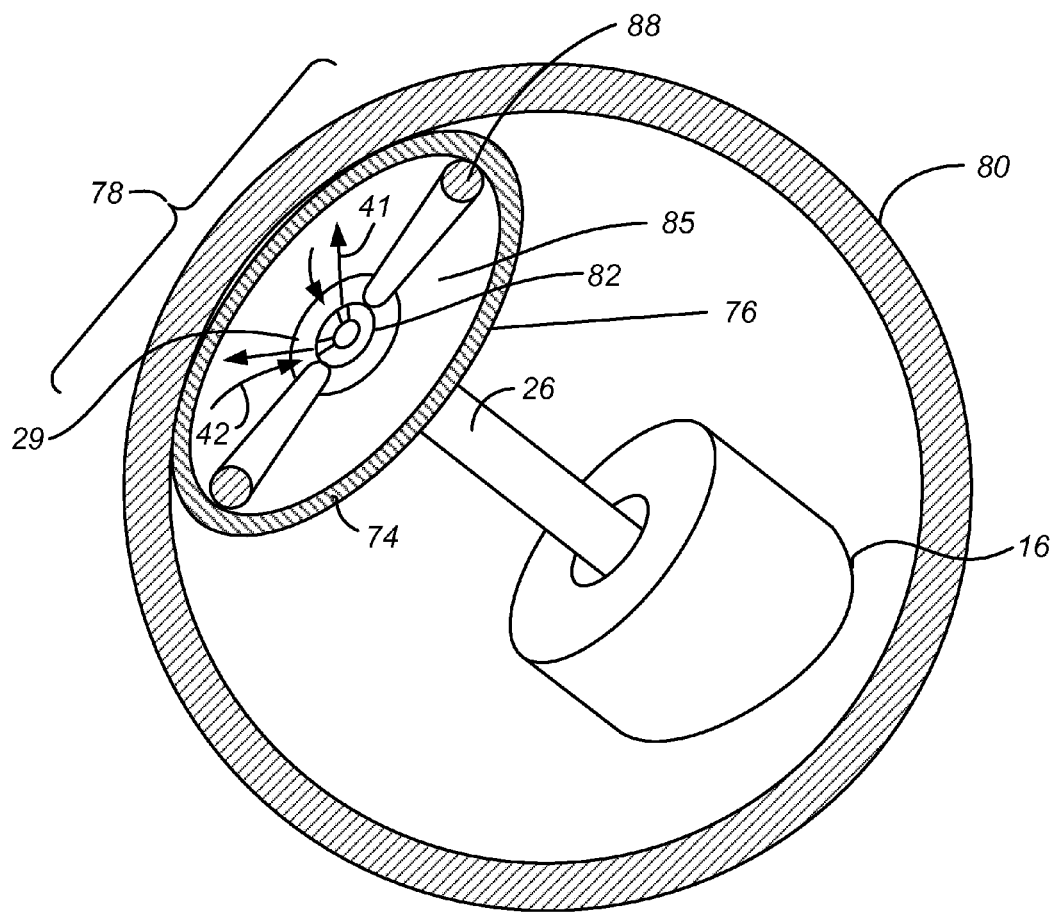

FIGS. 12 and 12A are simplified side and end cross-sectional views of a balloon type focal ablation system 70 in which a balloon type focal ablation assembly 72 is used with an endoscopic tube 16 of an endoscope 12. A balloon 74 is mounted to the distal end 34 of cryogenic catheter 26. The cryogenic catheter 26 extends through the channel 28 of endoscopic tube 16. The therapeutic region 36 is along a sidewall 76 of balloon 74. In this example cryogenic catheter 26 has a dogleg shape distal portion to facilitate placement of therapeutic region 36 along sidewall 76 and against a target treatment site 78 of the body structure 80. Delivery catheter 82 passes through lumen 29 with its distal end 84 secured to the distal end 86 of balloon 74. Delivery catheter 82 has, in this example, a number of laterally directed exit openings 41 acting as delivery ports to direct liquid refrigerant 40 into the interior 85 of balloon 74 and against sidewall 76 of balloon 74 at target site 78. The size, number and positions of openings 41 can be chosen according to the size of the target treatment site 78 and desired mass flow rate/surface area for refrigerant 40. FIG. 12A shows the use of reinforcing elements 88, such as nitinol support wires, within the balloon 74 to cause the balloon to have a flattened or oval cross-sectional shape to better conform to the shape of the body structure 80. The use of reinforcing elements 88 also helps to maintain balloon 74 in direct contact with the body structure during the procedure.

Figure 13:
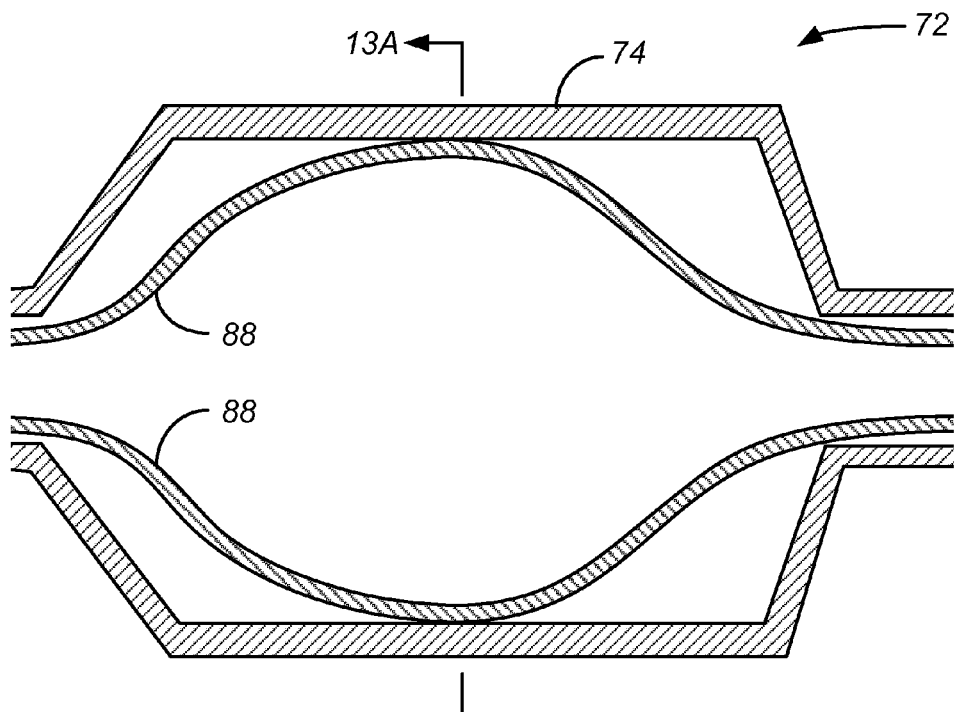
Figure 13A:
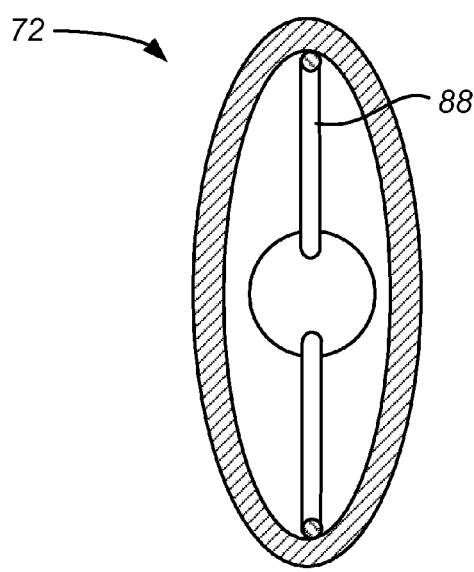

FIGS. 13 and 13A are simplified side and end cross-sectional views of a focal ablation balloon 74 and reinforcing elements 88 similar to those of FIGS. 12 and 12A.

Figure 14:
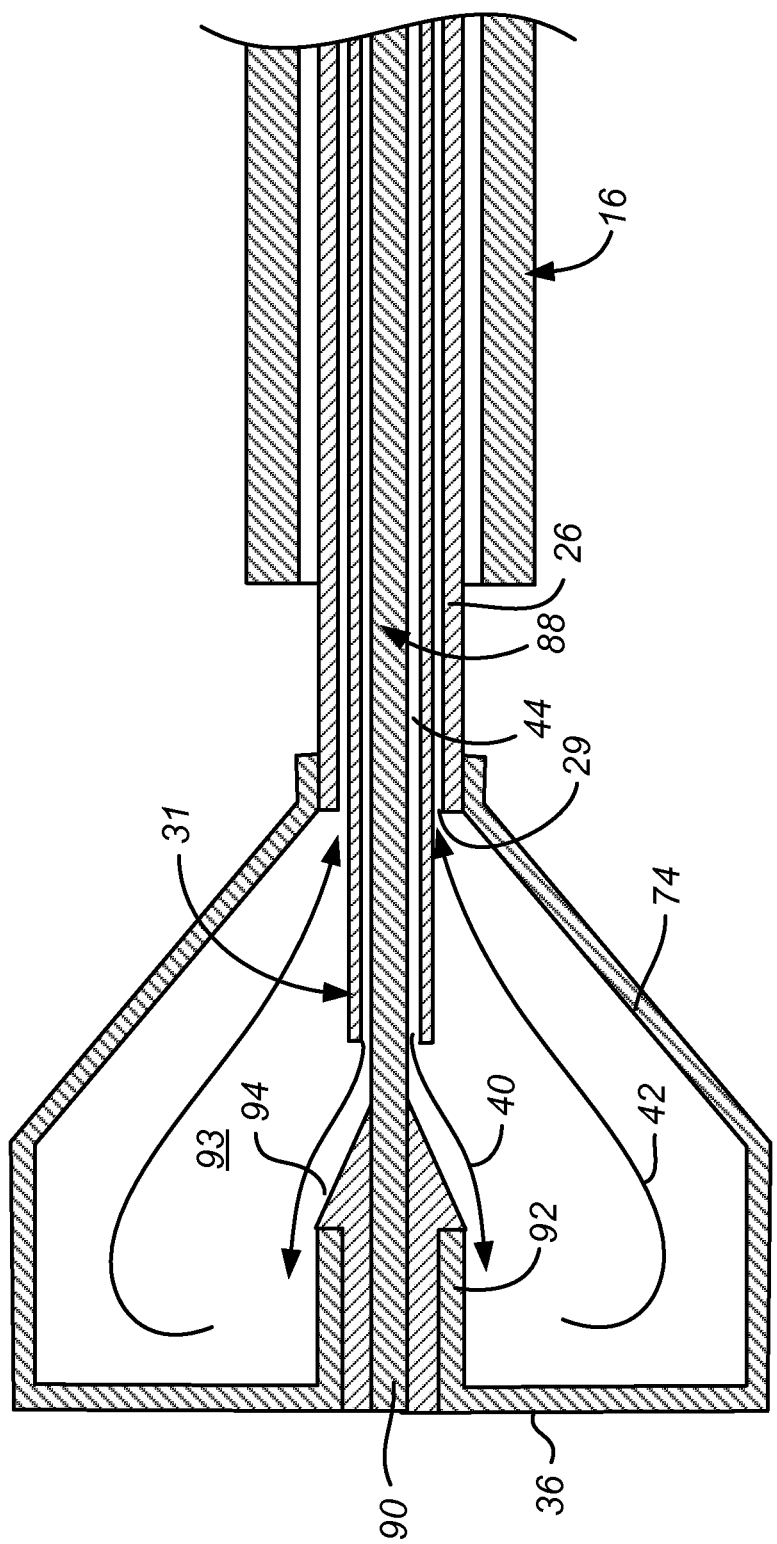

FIG. 14 illustrates another example of a balloon type focal ablation system 70 in which the distal end of the reinforcing element 88 extends through the delivery catheter 31. The distal end 90 of reinforcing element 88 is secured to the central portion of the working region 36 of balloon 74 in the following manner. Balloon 74 has a stem portion 92 at the center of therapeutic, working region 36 extending inwardly into the volume 93 defined by the balloon. A thermally conductive filler material 94 is used to secure distal end 90 of reinforcing element 88 to stem portion 92. As indicated by liquid refrigerant arrows 40, liquid refrigerant is directed toward the center of working region 36 surrounding stem portion 92.

Figure 15:
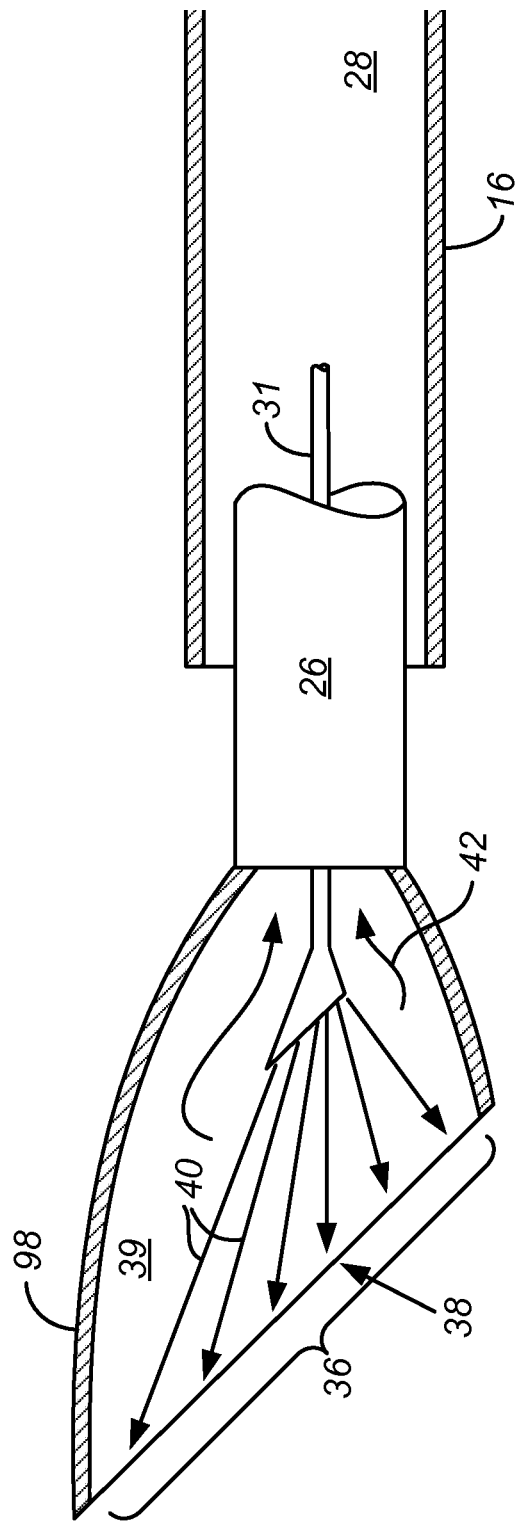

FIG. 15 shows an example of a balloon type focal ablation system comprising a balloon type cap 98, which is not generally rigid as caps 22 in the examples above FIGS. 1-11. Rather, cap 98 is typically made of one or more materials similar to those used with balloon 74 and includes reinforcing elements 88, not shown in FIG. 15, which may be made of, for example, a metal, such as nitinol, or of the same material as the rest of cap 98. Cap 98 also includes a cover 38, typically made of a thin film of silicone, polyurethane, or PET. As with the balloon type focal ablation systems 70 of FIGS. 12-14, the full expansion of cap 98 is typically the result of reinforcing elements 88 and the internal pressure created by the vaporization of refrigerant 40 and expansion due to the creation of exhaust gas 42.

In the use of the focal ablation system 70 of FIGS. 12-13A, the physician will typically select a focal ablation assembly 72 including a balloon 74 having the appropriate size and shape for the particular target treatment site 78. Cryogenic catheter 26, typically with delivery catheter 82 therein and the balloon 74 at the distal end 34, can be placed through accessory port 18 of the endoscope 12 and pass through channel 28 of the endoscopic tube 16 until sidewall 76 of balloon 74 is adjacent to therapeutic region 36 of body structure 80. The refrigerant 40 from cryoablation controller 25 is then directed through delivery catheter 82 and against balloon sidewall 76 at to the target treatment site 78. The evaporation of the refrigerant on sidewall 76 of balloon 74 lowers the temperature of the tissue at the target treatment site 78 enough to cause necrosis of the target tissue. The evaporated refrigerant 42 passes out of the interior of balloon 74 through catheter lumen 29. The use of the examples of FIGS. 14 and 15 are carried out in similar manners with the working region 36 positioned at target treatment site 78.

The above descriptions may have used terms such as above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims. For example, cryogenic catheter 26 may also contain features related to measuring the performance of the system for either safety or efficacy reasons. Examples of these features include a pressure sensing lumen for monitoring pressure in the volumes 39, 93, and a temperature sensing device (e.g. thermistor or thermocouple) for monitoring temperature in the cap 22, especially at working region 36.

Any and all patents, patent applications and printed publications referred to above are incorporated by reference.

What is claimed is:

1. A focal ablation assembly, adapted for use with an endoscope comprising an endoscopic tube having proximal and distal ends and defining a channel extending between the proximal and distal ends, the focal ablation assembly comprising:
    a cryogenic catheter placeable within the channel, the cryogenic catheter defining a catheter lumen and having a distal end placeable at the distal end of the endoscopic tube;
    a balloon mountable to the distal end of the catheter, the balloon extending distally of both of the distal ends of the endoscopic tube and the cryogenic catheter;
    the balloon placeable in collapsed and expanded states;
    a reinforcing element at least partially defining the shape of the balloon in the expanded state, the reinforcing element comprising a stiffening member adapted to extend along the endoscopic tube and having a distal end;
    the balloon comprising a thermally conductive therapeutic region;
    the balloon having a generally tubular stem portion, the stiffening member extending into and secured to the stem portion; and
    a thermally conductive filler material between the stiffening member and the stem portion.

2. The assembly according to claim 1, wherein the balloon is made of an elastomeric material.

3. The assembly according to claim 1, wherein the thermal conductivity of the balloon is greater at the therapeutic region than at least a portion of the remainder of the balloon.

4. The assembly according to claim 1, wherein the balloon has a distal end and the therapeutic region is at the distal end of the balloon.

5. The assembly according to claim 1, wherein the therapeutic region has a flat shape.

6. The assembly according to claim 1, wherein the therapeutic region has a cross-sectional area and the endoscopic tube has a cross-sectional area, the cross-sectional area of the therapeutic region being greater than the cross-sectional area of the endoscopic tube when the cryogenic catheter is located within the endoscopic channel.

7. The assembly according to claim 1, further comprising a delivery catheter extendable along the channel and having a distal portion fluidly coupled to the balloon interior, whereby refrigerant can be introduced into the balloon interior and towards the therapeutic region by the delivery catheter.

8. The assembly according to claim 7, wherein the refrigerant delivery catheter extends through the cryogenic catheter.

9. The assembly according to claim 7, further comprising an exhaust lumen defined by the catheter lumen.

10. The assembly according to claim 7, further comprising an exhaust lumen adapted for use within at least one of (1) the channel of the endoscopic tube, and (2) the catheter lumen.

11. A focal ablation assembly, adapted for use with an endoscope comprising an endoscopic tube having proximal and distal ends and defining a channel extending between the proximal and distal ends, the focal ablation assembly comprising:
    a cryogenic catheter placeable within the channel, the cryogenic catheter defining a catheter lumen and having a distal end placeable at the distal end of the endoscopic tube;
    a balloon mountable to the distal end of the catheter, the balloon extending distally of both of the distal ends of the endoscopic tube and the cryogenic catheter;
    the balloon placeable in collapsed and expanded states, the balloon having a balloon interior;
    a reinforcing element at least partially defining the shape of the balloon in the expanded state;
    the balloon defining a balloon volume when in the expanded state;
    the balloon comprising a thermally conductive therapeutic region, the thermally conductive therapeutic region providing effectively no thermal insulation;
    the reinforcing element comprising a stiffening member adapted to extend along the endoscopic tube and having a distal end;
    the therapeutic region of the balloon being secured to the distal end of the stiffening member;
    a central portion of the therapeutic region of the balloon having a generally tubular stem portion extending into the balloon volume;
    the stiffening member extending into and secured to the stem portion; and a thermally conductive filler material between the stiffening member and the stem portion.

* * * * *